United States Patent [19]

Shumiyashu

[11] Patent Number: 4,480,596
[45] Date of Patent: Nov. 6, 1984

[54] MAGNETIC ELASTIC LUMBAR BELT

[75] Inventor: Noriaki Shumiyashu, Tokyo, Japan

[73] Assignee: TDK Corporation, Tokyo, Japan

[21] Appl. No.: 31,914

[22] Filed: Apr. 20, 1979

[30] Foreign Application Priority Data

| Apr. 20, 1978 [JP] | Japan | 53-51437[U] |
|---|---|---|
| Apr. 20, 1978 [JP] | Japan | 53-51438[U] |
| Apr. 20, 1978 [JP] | Japan | 53-51439[U] |
| Aug. 30, 1978 [JP] | Japan | 53-118724[U] |

[51] Int. Cl.$^3$ ............................................. A61N 1/42
[52] U.S. Cl. .................................................. 128/1.3
[58] Field of Search ................................ 128/1.3–1.5, 128/574, 578; 2/237

[56] References Cited

U.S. PATENT DOCUMENTS

| 125,006 | 3/1872 | Bazault | 128/1.3 |
|---|---|---|---|
| 658,027 | 9/1900 | Steiger | 128/1.3 |
| 1,050,280 | 1/1913 | Krüger | 128/1.5 |
| 2,106,334 | 1/1938 | Adamson | 2/237 |
| 2,112,892 | 4/1938 | Hardie et al. | 2/237 |
| 2,195,894 | 4/1940 | Moore | 2/237 |
| 3,885,383 | 5/1975 | Tanaka | 59/79 |
| 3,943,912 | 3/1976 | Nakayama | 128/1.3 |
| 4,095,587 | 6/1978 | Ishikawa | 128/1.3 |
| 4,162,672 | 7/1979 | Yazaki | 128/1.3 |
| 4,197,840 | 4/1980 | Beck et al. | 128/1.3 X |

FOREIGN PATENT DOCUMENTS

| 259271 | 10/1963 | Australia | 128/1.3 |
|---|---|---|---|
| 995367 | 8/1951 | France | 128/1.3 |
| 288 | of 1872 | United Kingdom | 128/1.3 |
| 15987 | of 1884 | United Kingdom | 128/1.3 |
| 11816 | of 1887 | United Kingdom | 128/1.3 |

Primary Examiner—Kyle L. Howell
Assistant Examiner—John C. Hanley
Attorney, Agent, or Firm—Armstrong, Nikaido, Marmelstein & Kubovcik

[57] ABSTRACT

A magnetic belt for medical purposes, which exposes the lumbar portion of a human body with magnetic flux has been found. The magnetic belt comprises an elastic belt body, a flexible sheet removably and slidably mounted on the belt body, and a plurality of permanent magnets removably mounted in said sheet. The belt body is made of elastic cloth and the coefficients of elasticity differs breadthwise. The sheet is made of flexible plastic, such as ABS (Acryl-Butadiene-Styrene), having a plurality of circular holes for accepting the permanent magnets. Each permanent magnet is mounted in a plastic housing or a capsule having a flange which engages with the edge of the hole of said sheet. The permanent magnet is, for instance, an alloy of samarium and cobalt with a surface magnetic flux of approximate 1,200 gauss. The present magnetic belt is, when attached on the lumbar portion, effective for reducing stiffness or pain in the muscles of the human body.

10 Claims, 17 Drawing Figures

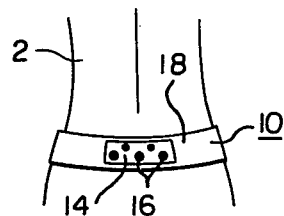
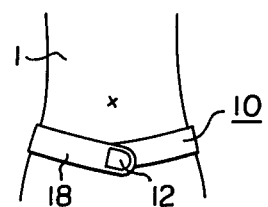
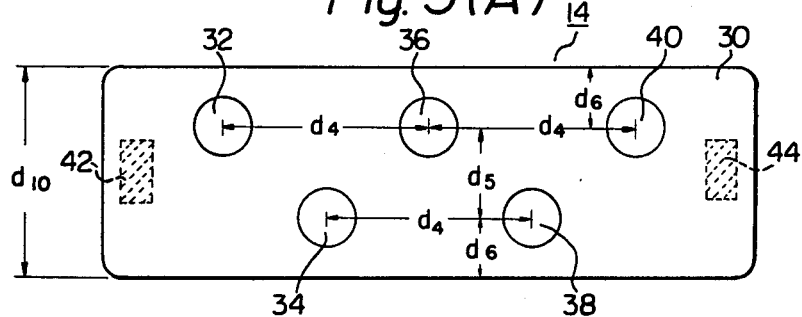
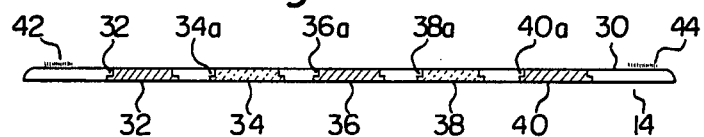
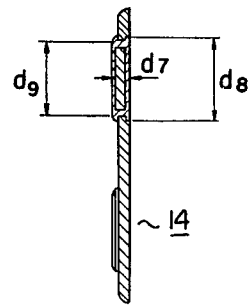

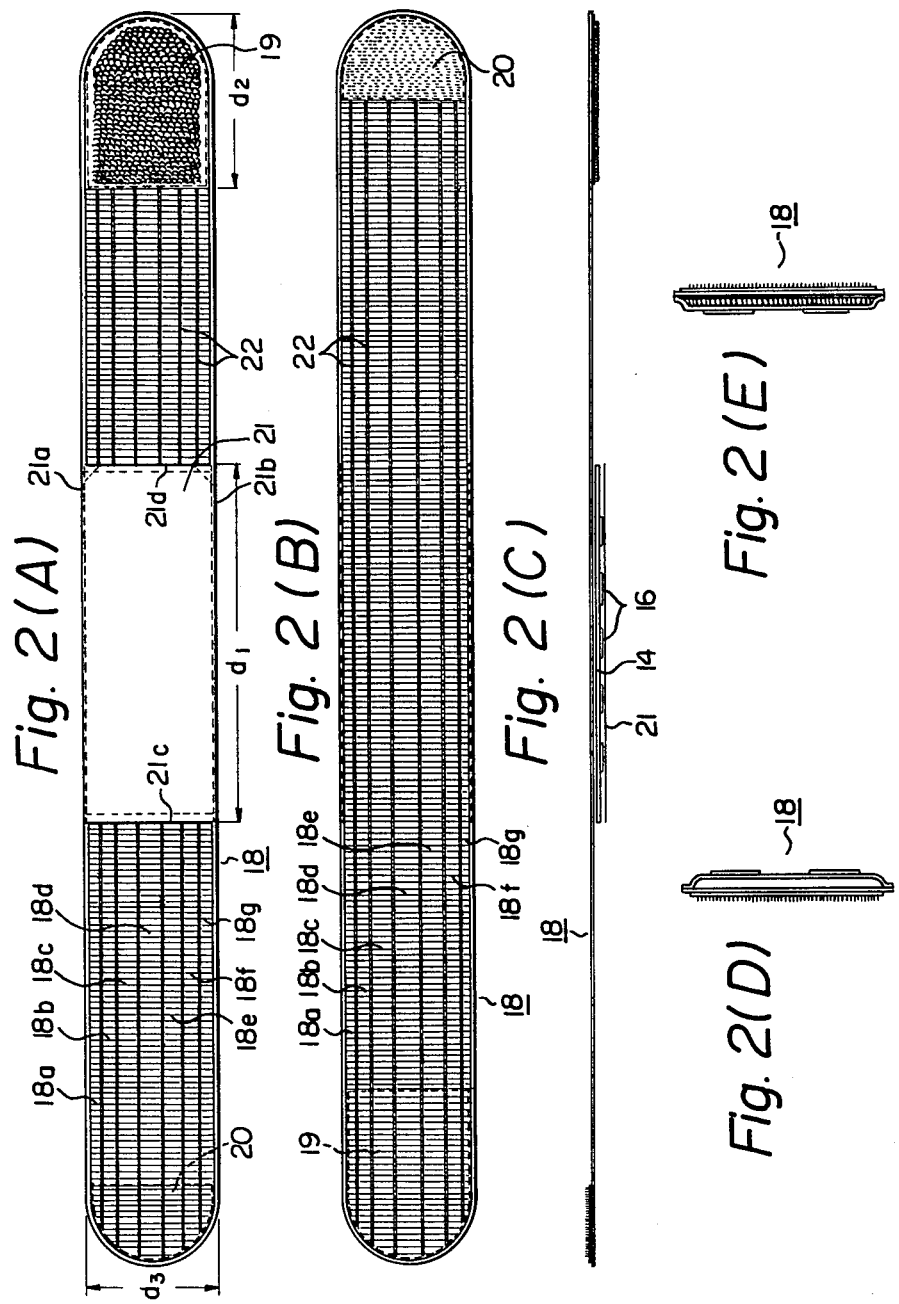

MAGNETIC ELASTIC LUMBAR BELT

BACKGROUND OF THE INVENTION

The present invention relates to a magnetic belt for medical purposes, in particular, relates to a magnetic lumbar belt for applying magnetic flux to the lumbar region between waist and hips of a human body.

It has been well known that the application of magnetic flux to a human body is effective for promoting health and well being, reducing stiffness or pain in the shoulders and/or low back pain syndrome, and for improving the blood circulation, although the theoritical analysis of those effects is still unknown. In particular, it has been known that a magnetic necklace is effective for the treatment of stiffness in the shoulders. Concerning the low back pain syndrome, there is a report entitled "Treatment of low back pain syndrome by use of magnetic lumbar band" published by Department of Orthopaedic Surgery & Rehabilitation Center, Jichi Medical School in Japan. The report states that among 50 patients the magnetic lumbar band was effective with 31 patients for reducing low back pain. That is to say, the magnetic lumbar belt is effective for 62% of patients. The effect appears in the patients within about one week when they wear the magnetic lumbar belt. Further the patients felt a warmness around the lower back. Of course no ill effects were observed.

A prior magnetic lumbar belt has an elastic belt body made of cloth, and a plurality of solid permanent magnets unremovably sewn in the belt body.

However, said prior magnetic lumbar belt has the following disadvantages.

First, a prior belt applies very uneven pressure to the human body and is uncomfortable to wear. This is due to the fact that the contours of the upper and lower parts of the lumbar zone of the human body differ widely. Because of these differences in contour, certain parts of the belt made of ordinary rubber blended yarn fail to tightly fit the human body. Further, because the prior belt does not provide uniform elasticity throughout the whole width of the belt, various parts of the lumbar zone do not receive a uniformly tight fit, resulting in discomfort and improper application of the magnetic flux.

Next, it is necessary that the magnet can be changed in order to adjust the strength of the magnetic flux. However, the change of a magnet is impossible in the prior magnetic lumbar belt since the prior magnet is sewn into the belt body and is unremovable. Further, in a prior magnetic belt it is impossible to adjust or control the number of permanent magnets or the portion of the human body to be exposed.

SUMMARY OF THE INVENTION

It is an object, therefore, of the present invention to overcome the disadvantages and limitations of a prior magnetic lumbar belt by providing a new and improved magnetic lumbar belt.

Another object of the present invention is to provide a magnetic lumbar belt in which the belt body fits smoothly with the human body providing comfort and uniform application of the magnetic flux.

Still another object of the present invention is to provide a magnetic lumbar belt in which the number of permanent magnets attached to the belt can be easily changed, and the position at which the permanent magnets are attached is also adjustable.

The above and other objects are attained by a magnetic lumbar belt comprising an elongated elastic belt having a pocket approximately at the center of the belt and means for looping the same at the ends, a flexible sheet having a plurality of holes with flanges inserted in said pocket, a plurality of magnet capsules each of which is removably engaged with the flange of said holes of the sheet, each of the magnet capsules having a disk-shaped permanent magnet and a flexible plastic capsule covering the magnet. Preferably, the permanent magnet is an alloy of samarium and cobalt, approximate 15 mm in diameter and approximate 2 mm in thickness.

BRIEF DESCRIPTION OF THE DRAWINGS

The foregoing and other objects, features, and attendant advantages of the present invention will be appreciated as the same become better understood by means of the following description and accompanying drawings wherein;

FIG. 1(A) and FIG. 1(B) show the magnetic belt according to the present invention worn on a human body, FIG. 2(A), FIG. 2(B), FIG. 2(C), FIG. 2(D) and FIG. 2(E) show the structure of the belt body according to the present invention, FIG. 3(A), FIG. 3(B) and FIG. 3(C) show the embodiment of the flexible sheet according to the present invention.

DESCRIPTION OF THE PREFERRED EMBODIMENTS

Figure 4:
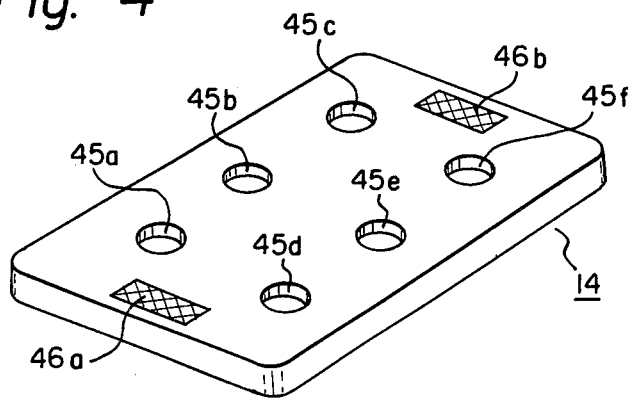
FIG. 4 shows the other embodiment of the flexible sheet according to the present invention.

FIG. 1(A) and FIG. 1(B) show the magnetic lumbar belt 10 which is worn on a human body. As shown in those figures, the magnetic belt 10 is attached around the lumbar portion of the human body with the end 12 buttoned, snapped, or Velcro closed at the front portion 1 of the human body. At the back portion 2 of the human body, a plurality of solid permanent magnets 16 removably attached to the magnetic sheet 14 are also removably attached to the belt body so that the magnetic flux from the magnets can be applied to the low back or the back lumbar portion. In the embodiments of those figures, five permanent magnets 16 are utilized, and preferably those magnets are positioned symmetrically with the spinal column. As apparent from the figures, the present magnetic belt has a belt body made of elastic textile, a magnetic sheet slidably inserted in the pocket of the belt body, and some permanent magnets removably attached to the sheet. Each of these features will be explained in detail hereinafter.

A belt body 18 is shown in FIGS. 2(A) through 2(E), in which FIG. 2(A) is the front view of the belt, FIG. 2(B) is the back view of the belt, FIG. 2(C) is the plane view of the belt, FIG. 2(D) is the left side view of the belt, and FIG. 2(E) is the right side view of the belt.

The belt body 18 comprises a plurality of elongated elastic belt elements 18a, 18b, 18c, 18d, 18e, 18f and 18g, each of which is connected by thin warp yarns. The width of those belt elements is not uniform but depends upon their location in the lateral direction of the belt. Preferably, the width of the belt element is large at the center of the belt body (18c, 18d, 18e) and is small at the peripheral portion of the belt (18a, 18b, 18f, 18g) as shown in the figures. At both the extreme ends of the belt body 18, means is provided for connecting both the ends of the same, and said means can be a button, a snap, or a Velcro fastener. The embodiment in FIG. 2(A) through FIG. 2(E) shows the Velcro fastener, in which a Velcro male 19 and a Velcro female 20 are provided at each end of the belt body so that the belt fits on the lumbar portion of the human body. At the center portion of the belt 18, there is provided a pocket covered with a cover cloth 21. The upper line 21a and the bottom line 21b of the cover cloth 21 are sewn to the belt body 18. However, the side lines 21c and/or 21d are not sewn to the belt body and provide an opening. Therefore, the magnetic sheet 14 having a plurality of permanent magnets 16 can be removably inserted in the pocket composed of the belt body and the cover cloth through said opening.

Each of the belt elements 18a through 18g shall be blended with rubber yarns to impart elasticity in the horizontal direction or shall be elastic yarns. Or alternatively, the fabric construction itself shall be such that elasticity is imparted to the cloth lengthwise. Therefore, when the duration that the woof yarn is drawn out is properly designed, that is to say, when the width of each belt element 18a through 18g is properly designed, the coefficient of elasticity of the belt body should become different breadthwise. As apparent from FIG. 2(A) and FIG. 2(B), the width of the belt element is large at the center of the belt, and is small at the upper and lower portions of the belt. Therefore, when the belt is stretched, the central zone is less stretched than the border zones. Therefore, the belt body will be fit tightly and comfortably to every part of the lumbar zone, and the belt will be firmly and uniformly tight on each part of the lumbar zone providing comfort of wear. Since permanent magnets are properly distributed on the center portion of the belt, they are also closely applied to every part of the lumbar zone, providing effective application of the magnetic flux.

It should be noted in FIG. 2(A) through FIG. 2(E), that the surface shown in FIG. 2(A) is the inner side which contacts the skin of the human body and the surface shown in FIG. 2(B) is the outer side.

According to the preferable embodiment, the size of the belt is as follows; the length $d_1$ of the pocket is 20 cm, the length of the Velcro portion 19 is $d_2 = 15$ cm, the width $d_3$ of the belt is $d_3 = 7$ cm, and the whole length of the belt can be designed according to the size of the human body.

Next, the structure of the magnetic sheet 14 will be described in accordance with FIGS. 3(A), 3(B) and 3(C), and FIG. 4. FIGS. 3(A), 3(B) and 3(C) show the first embodiment of the sheet according to the present invention, in which FIG. 3(A) shows the plane view, FIG. 3(B) shows the vertical view and FIG. 3(C) shows the cross sectional view. The sheet 14 comprises a flexible plastics board 30 which has a plurality of circular holes 32, 34, 36, 38 and 40. The sheet is made of for instance, ABS plastics (Acryl-Butadiene-Styrene), and the sheet 14 may have means 42 and 44 for fixing the sheet to the belt body. Those means 42 and 44 are for instance a Velcro fastener, a button, or a snap. The circular holes 32 through 40 are for accepting a magnet capsule, and for that purpose each hole has a circular flange 32a, through 40a. A magnet capsule can engage with that flange, and thus, a magnet capsule is removably mounted in said hole. According to the preferable embodiment, the sizes $d_4$ through $d_{10}$ of the sheet are as follows. The $d_4$ which is the length between two adjacent holes in horizontal direction is $d_4 = 6$ cm, the $d_5$ which is the vertical length between holes is $d_5 = 3$ cm, the $d_6$ which is the length between the center of the hole and the edge of the sheet is $d_6 = 1.5$ cm, the width $d_7$ of a magnet capsule is $d_7 = 0.4$ cm, the outer diameter $d_8$ of the hole is $d_8 = 19.3$ mm, the inner diameter $d_9$ of the hole is $d_9 = 17.3$ mm, and the width $d_{10}$ of the sheet is 6 cm.

FIG. 4 shows the other structure of the magnetic sheet 14, in which six holes 45a through 45f are provided for accepting a magnet capsule removably, and Velcro fasteners 46a and 46b are provided for fixing the sheet to the belt body.

Figure 5:
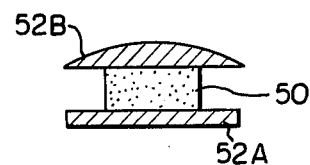
FIG. 5 shows the structure of the magnetic capsule according to the present invention.

Next, the structure of a magnet capsule will be described in accordance with FIG. 5, and FIGS. 6(A) and 6(B). FIG. 5(A) shows the first embodiment of the magnet capsule according to the present invention, in which a disk shaped permanent magnet 50 and a pair of flexible circular chips 52A and 52B are provided. The diameter of those chips is a little larger than the diameter of the magnet 50 so that the assembled magnet capsule is fixed in the hole of the sheet. The chips are made of, for instance, soft polyethylene. The lower chip 52A is flat, and the upper chip 52B has a thick portion at the center of the same like an optical lens. The curved surface of the upper chip 52B faces with the human body. The chips are bonded to the magnet 50.

Figure 6:
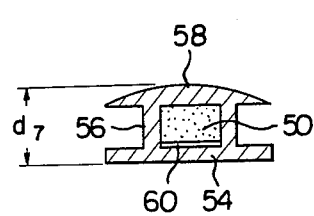
FIG. 6(A) and FIG. 6(B) show the structure of the other magnetic capsule according to the present invention.
Figure 6:
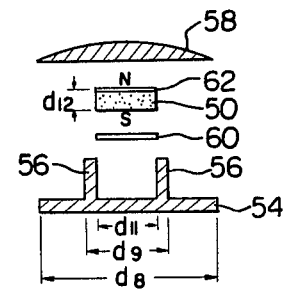

FIG. 6(A) shows the other structure of a magnet capsule and FIG. 6(B) is the assembly drawing of the same. The magnet capsule in FIGS. 6(A) and 6(B) comprises a permanent magnet 50, a magnetic shield plate 60, a coating 62, a cylinder 56 surrounding the magnet 50 with the shield plate 60 and the coating 62, and a pair of chips 54 and 58. The shield 60 is provided for preventing leakage of the magnetic flux outside the magnetic belt and said shield 60 is made of a ferromagnetic material like iron. The coating 62 is for decoration of the magnet and is for instance gold color. Of course the coating 62 can be replaced by appropriately decorated paper. The surface of the upper chip 58 is curved as shown in the drawing. The upper and lower chips 58 and 54, and the cyclindrical tube 56 are made of flexible plastics like soft polyethylene. In assembling the magnet capsule in FIGS. 6(A) and 6(B), the flat chip 54 with the cylindrical tube 56 at the center of the same is first prepared. Then, the magnetic shield disk 60 and the permanent magnet 50 with the coating 62 are inserted in said cylindrical tube. Next, the upper chip 58 is attached to the upper end of the tube 56 through, for instance, ultrasonic-wave bonding, in which an ultrasonic-wave energy generates heat between the upper chip 58 and the upper end of the tube 56, and the heated portions are melted thus the upper chip 58 is thermocoupled with the tube 56. Of course the curved dhip 58 faces the human body.

According to the preferred embodiment of the present invention, the size of each portion of the magnet capsule is as follows. The diameter $d_8$ of the chips 54 and 58 is $d_8 = 19.3$ mm which is the same as $d_8$ described in FIG. 3(C). The outer diameter $d_9$ of the cylindrical tube 56 is $d_9=17.3$ mm, which is the same as $d_7$ in FIG. 3(C). The inner diameter $d_{11}$ of the tube 56, which is the same as the diameter of the permanent magnet 50, is 15 mm. The thickness $d_{12}$ of the permanent magnet 50 is 2 mm. And the thickness $d_7$ of the capsule itself is $d_7=4$ mm, which is the same as $d_7$ in FIG. 3(C).

The permanent magnet 50 is magnetized in the axial direction. The polarity of the magnet can be arbitrary. That is to say, the upper surface of the magnet which confronts with a human body can be either N-pole or S-pole. The strength of the magnetic flux by the magnet is in the range from 500 to 2,000 gauss and is preferably about 1,200 gauss at the surface of the magnet. However, due to the presence of the magnetic shield 60, the strength of the magnetic flux at the lower chip 54 is decreased approximate to 400–500 gauss.

The permanent for the present magnet belt can be, for instance, an alloy of samarium and cobalt, comprising samarium 36% in weight and cobalt 64% in weight. The manufacturing process of that SmCo magnet is as follows. First, the raw material is combined and powdered, then, is molded in a desired shape in an atmosphere having magnetic flux. Then, the shaped mold is sintered in an argon gas atmosphere at approximate 1150° C. for one hour. Next, a stepwise cooling process which cools the product with a controlled stepwise temperature is performed for one hour. After the mold is completely cooled, the magnetizing process is performed and permanent magnet of SmCo is obtained. The approximate weight of a permanent magnet thus produced and having the aforementioned size (15 mm of diameter and 2 mm of thickness) is approximate 14.8 gramm.

Figure 7:
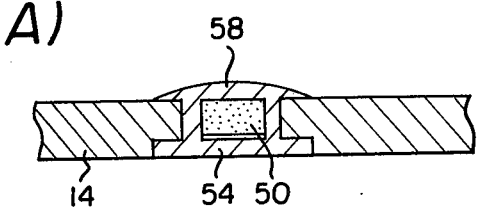
FIG. 7(A), FIG. 7(B), and FIG. 7(C) show some embodiments of the engagement of the magnetic capsule with the magnetic sheet.
Figure 7B:
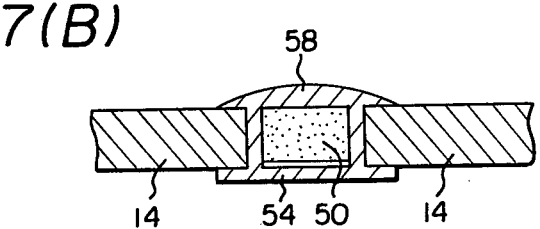
Figure 7C:
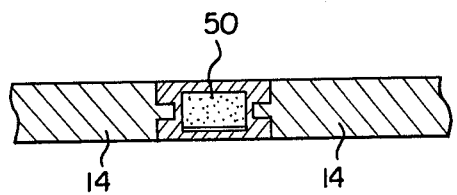

FIG. 7(A), FIG. 7(B) and FIG. 7(C) show some embodiments of inserting a magnet capsule in the sheet.

FIG. 7(A) shows the embodiment that the lower portion of the magnet capsule is flat with the sheet 14 and the upper portion of the magnet capsule is convex from the sheet.

FIG. 7(B) shows the embodiment that both the upper and the lower portions of the magnet capsule are convex from the sheet.

FIG. 7(C) shows the embodiment that both the upper and the lower portions of the magnet capsule are flat with the sheet.

Practically, there is an opinion that the surface which confronts the human body should be convex so that the magnet can fit the human body with some pressure. In this sense, the embodiments in FIGS. 7(A) and 7(B) are desirable. On the other hand, as the magnetic belt is cloth, a flat configuration is desirable to keep a slim line.

It should be appreciated that magnet capsule shown in FIGS. 7(A) through 7(C) is removable from the sheet, since both the sheet and the capsule are made of flexible plastics The removable magnet capsule is the important feature of the present invention, and by exchanging a magnet capsule, the strength of the magnetic flux applied to the human body can be adjusted to a desired value.

Further, since the magnetic sheet is slidable in the pocket of the belt body, the portion that the magnetic flux is applied to is adjustable.

As described in detail, the magnetic lumbar belt according to the present invention can fit comfortably with the contour of the human body, the position of a magnet and the number of magnets are adjustable, and further, the strength of a magnet is also adjustable. Accordingly, the most convenient and effective medical treatment is obtained.

From the foregoing it will now be apparent that a new and improved magnetic lumbar belt has been found. It should be understood of course that the embodiments disclosed are merely illustrative and are not intended to limit the scope of the invention. Reference should be made to the appended claims, therefore, rather than the specification as indicating the scope of the invention.

What is claimed is:

1. A magnetic elastic lumbar belt comprising an elongated elastic belt having a pocket with an opening therein, said pocket being positioned approximately at the center of the belt and means for looping the said belt at both ends thereof, a flexible sheet having a plurality of holes therethrough, removably inserted in said pocket through the opening therein, wherein each of said holes has a flange extending from the side of the hole towards the center thereof, a plurality of magnet capsule means each of which is removably engaged with the flange of said hole of the sheet, each of the magnet capsule means having a disk shaped permanent magnet and a flexible capsule surrounding the magnet, wherein said flexible capsule has a groove means therein for engaging said flange and wherein said magnet capsule means are removable from said sheet by deforming said flexible capsules surrounding the magnets.

2. A magnetic lumbar belt according to claim 1, wherein said belt comprises a plurality of elastic belt elements, the width of which are larger at the center of the belt and smaller at the peripheral portion of the belt, thus, the coefficient of elasticity is different in the lateral direction.

3. A magnetic lumbar belt according to claim 1, wehrein said sheet has five holes for accepting magnetic capsules.

4. A magnetic lumbar belt according to claim 1, wherein said sheet has six holes for accepting magnet capsules.

5. A magnetic lumbar belt according to claim 1, wherein said sheet is made of ABS plastics.

6. A magnetic lumbar belt according to claim 1, wherein said permanent magnet is made of an alloy of samarium and cobalt.

7. A magnetic lumbar belt according to claim 1, wherein said capsule is made of soft polyethylene.

8. A magnetic lumbar belt according to claim 1, wherein said permanent magnet has a size of approximate 15 mm in diameter and approximate 2 mm in thickness, and is magnetized approximately to 1,200 gauss at the surface of the same in the axial direction.

9. A magnetic lumbar belt according to claim 1, wherein said magnet capsule further comprises a magnetic shield at one side of the permanent magnet.

10. A magnetic sheet comprising a flexible sheet having a plurality of holes, each of said holes having a flange, extending from the side of the hole towards the center thereof, a plurality of magnet capsules each of which is detachably engaged with the flange of said hole of the sheet, each of the magnet capsules having a disk shaped permanent magnet and a flexible capsule covering the magnet and a groove means in said capsule, said permanent magnet being made of an alloy of samarium and cobalt, and said capsule being made of soft polyethylene, whereby said magnet capsules are detachable from said sheet by deforming said flexible capsules surrounding the magnets.

* * * * *